United States Patent [19]

Callahan

[11] Patent Number: Plant 7,332

[45] Date of Patent: Sep. 18, 1990

[54] CHRYSANTHEMUM PLANT NAMED SALMON SPLENDOR

[75] Inventor: Betty C. Callahan, Waleska, Ga.

[73] Assignee: Callahan's Greenhouses, Inc., Waleska, Ga.

[21] Appl. No.: 365,473

[22] Filed: Jun. 13, 1989

[51] Int. Cl.[5] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Salmon Splendor particularly characterized by its flat capitulum form, daisy capitulum type, salmon-pink ray floret color, diameter across face of capitulum of up to 14 cm at maturity when grown as a pinched disbudded pot mum, uniform nine week photoperiodic flowering response to short days, medium plant height when grown as a pinched pot mum, and upright branching pattern.

3 Drawing Sheets

The present invention comprises a new and distinct cultivar of Chrysanthemum, botanically known as *Dendranthema grandiflora*, and referred to by the cultivar name Salmon Splendor.

Salmon Splendor, identified as 78-66I-09, is a spontaneous mutation of the cultivar Splendor, disclosed in U.S. Plant Pat. No. 5,225, and was selected to expand the color range of the parental variety.

Salmon Splendor was discovered and selected by Betty C. Callahan as one flowering plant within a flowering block of Splendor in December of 1985, in a controlled environment in Waleska, Ga.

The first act of asexual reproduction of Salmon Splendor was accomplished when vegetative cuttings were taken from the initial selection in March of 1986 in a controlled environment in Waleska, Ga., by technicians working under formulations established and supervised by Betty C. Callahan.

Horticultural examination of controlled flowerings of successive plantings has shown that the unique combination of characteristics as herein disclosed for Salmon Splendor are firmly fixed and retained through successive generations of asexual reproduction.

Salmon Splendor has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions, which approximate those generally used in commercial greenhouse practice.

The following traits have been repeatedly observed and are determined to be basic characteristics of Salmon Splendor, which, in combination, distinguish this Chrysanthemum as a new and distinct cultivar:

1. Flat capitulum form.
2. Daisy capitulum type.
3. Salmon-pink ray floret color.
4. Diameter across face of capitulum up to 14 cm at maturity, when grown as a pinched disbudded pot mum.
5. Uniform nine week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Upright branching pattern.

The accompanying photographic drawings show typical inflorescence and leaf characteristics of Salmon Splendor, with the colors being as nearly true as possible with illustrations of this type. Sheet 1 is a color photograph of Salmon Splendor grown as a pinched disbudded pot mum. Sheet 2 is a black and white photograph of three views of the inflorescence of Salmon Splendor. Sheet 3 is a black and white photograph showing the upper and under sides of the leaves of Salmon Splendor at three stages of development (mature, intermediate and immature).

Of the commercial cultivars known to the inventor, the most similar in comparison to Salmon Splendor is the parent cultivar Splendor. All traits of Salmon Splendor are similar to those of Splendor, except the color of ray florets. The color of the ray florets of Salmon Splendor is salmon-pink, as contrasted with the light lavender ray florets of Splendor.

In the following description color references are made to The Royal Horticultural Society Colour Chart. The color values were determined on plant material grown as a pinched disbudded pot mum in Salinas, Calif. on Dec. 27, 1988.

Classification:

*Botanical.*—*Dendranthema grandifora* cv Salmon Splendor.

*Commercial.*—Daisy disbudded pot mum.

I. Inflorescence:

A. *Capitulum.*—Form: Flat. Type: Daisy. Diameter across face: Up to 14 cm at maturity.

B. *Corolla of ray florets.*—Color (generally tonality from a distance of three meters): Salmon-pink. Color (upper surface): Between 56A and 62C when fully mature; immature flowers tinged with 49C. Color (under surface): Closest to 36B to 36D. Shape: Flat, oblong.

C. *Corolla of disc florets.*—Color (mature): Closest to 6A to 6B. Color (immature): Color to 144C.

D. *Reproductive Organs.*—Androecium: Present on disc florets only; scant pollen. Gynoecium: Present on both ray and disc florets.

II. Plant:

A. *General Appearance.*—Height: Medium; 25 to 35 cm as a pinched pot mum with 0 to 7 long days after pinch prior to short days and 1 application of 2500 ppm B-9 SP. Branching pattern: Upright.

B. *Foliage.*—Color (upper surface): 147A. Color (under surface): 147B. Shape: Lobed and slightly serrated.

I claim:

1. A new and distinct Chrysanthemum plant named Salmon Splendor, as described and illustrated.

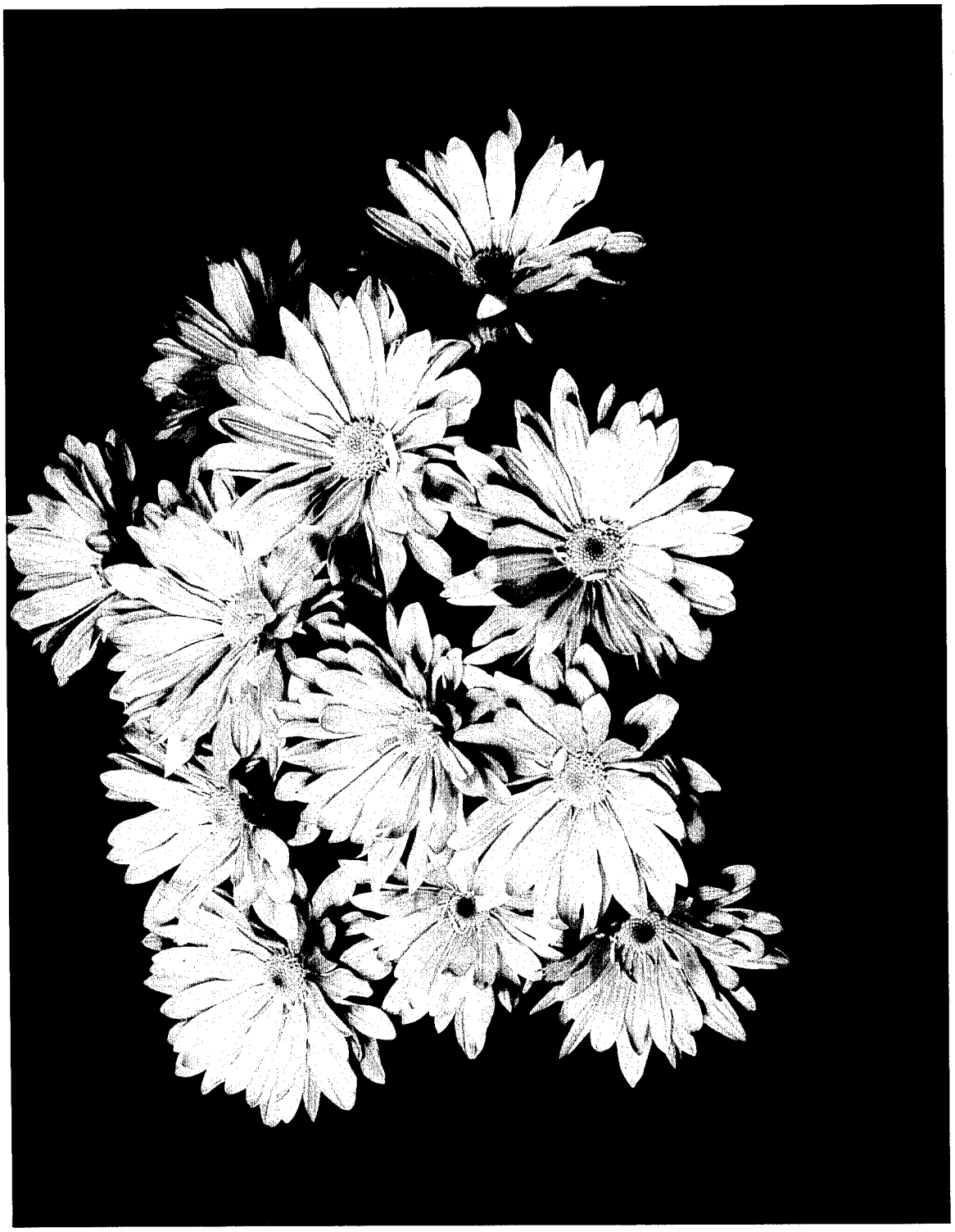

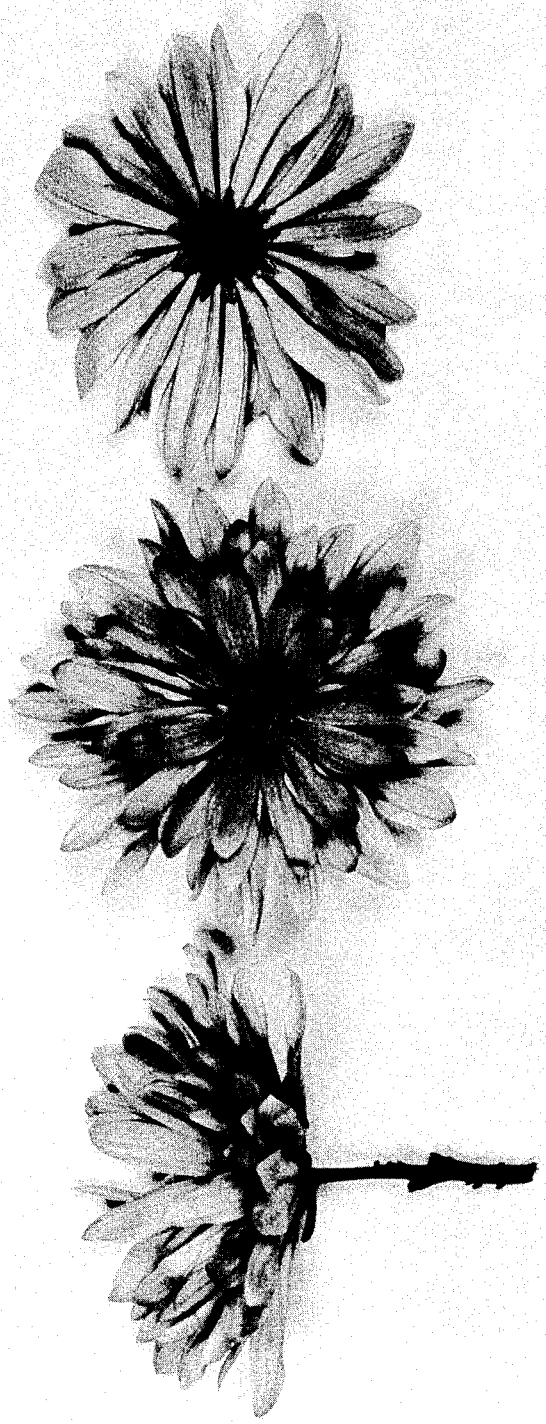

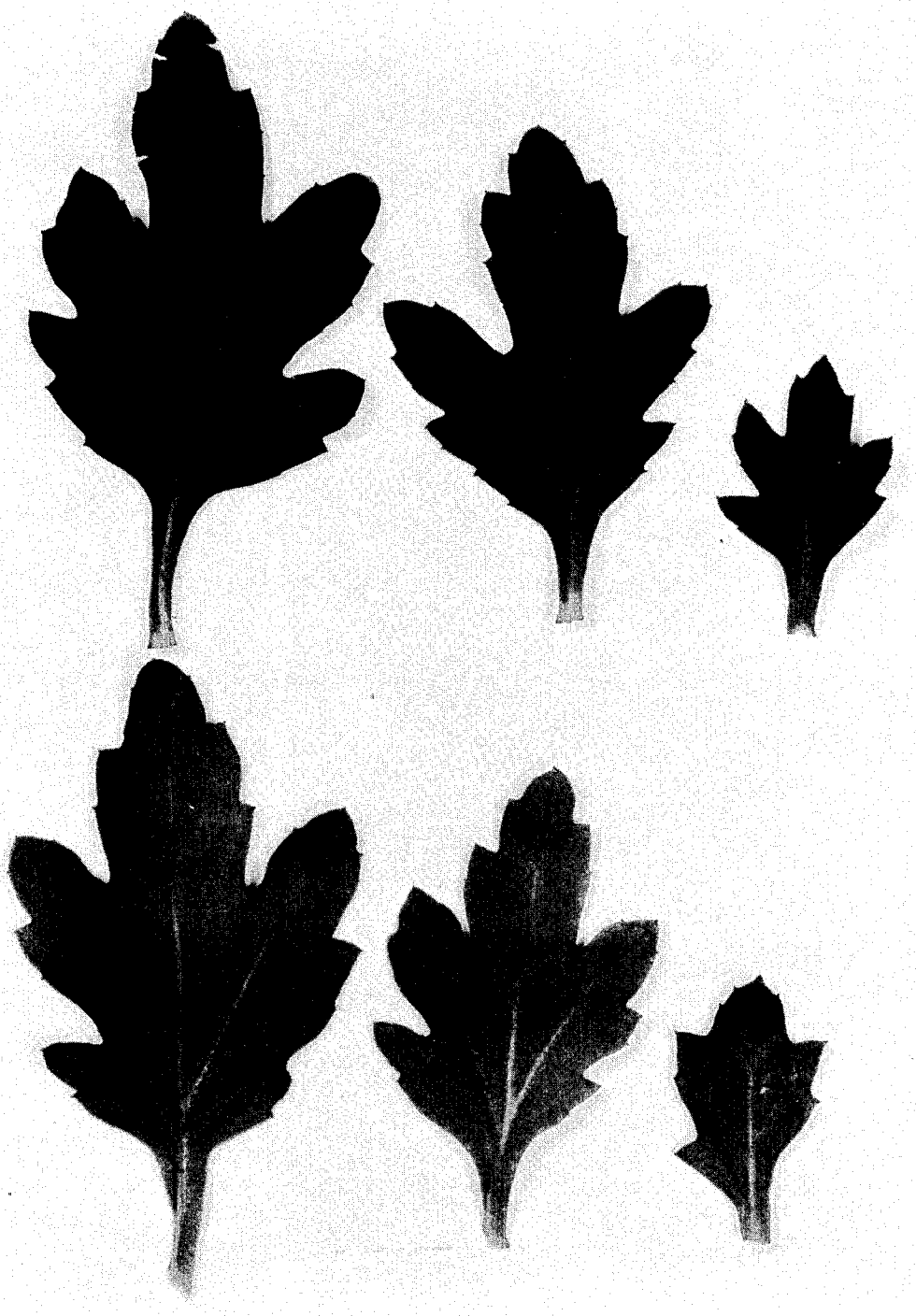

* * * * *